United States Patent
Yu et al.

(10) Patent No.: US 12,079,907 B2
(45) Date of Patent: Sep. 3, 2024

(54) SYSTEMS AND METHODS FOR MULTI-KERNEL SYNTHESIS AND KERNEL CONVERSION IN MEDICAL IMAGING

(71) Applicant: Mayo Foundation for Medical Education and Research, Rochester, MN (US)

(72) Inventors: Lifeng Yu, Byron, MN (US); Andrew D. Missert, Rochester, MN (US); Shuai Leng, Rochester, MN (US); Cynthia H. McCollough, Byron, MN (US); Joel G. Fletcher, Oronoco, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 471 days.

(21) Appl. No.: 17/280,980

(22) PCT Filed: Sep. 30, 2019

(86) PCT No.: PCT/US2019/053756
§ 371 (c)(1),
(2) Date: Mar. 29, 2021

(87) PCT Pub. No.: WO2020/069489
PCT Pub. Date: Apr. 2, 2020

(65) Prior Publication Data
US 2021/0358183 A1 Nov. 18, 2021

Related U.S. Application Data

(60) Provisional application No. 62/738,764, filed on Sep. 28, 2018.

(51) Int. Cl.
*G06K 9/00* (2022.01)
*A61B 6/00* (2006.01)
(Continued)

(52) U.S. Cl.
CPC .......... *G06T 11/008* (2013.01); *A61B 6/5258* (2013.01); *G06F 18/214* (2023.01);
(Continued)

(58) Field of Classification Search
CPC ............. G06T 11/008; G06T 2211/424; A61B 6/5258; G06F 18/214; G06F 18/217;
(Continued)

(56) References Cited

U.S. PATENT DOCUMENTS 7,920,669 B2 4/2011 Krauss
8,805,042 B2 8/2014 Weiss
(Continued)

FOREIGN PATENT DOCUMENTS

CN 1504931 A * 6/2004 ............... A61B 6/03
CN 107392868 A 11/2017
(Continued)

OTHER PUBLICATIONS

Cynthia H. McCollough, Low-dose CT for the detection and classification of metastatic liver lesions, Medical Physics, 44 (10), Oct. 2017.*
(Continued)

*Primary Examiner* — Xin Jia
(74) *Attorney, Agent, or Firm* — Quarles & Brady LLP (57) ABSTRACT

Systems and methods are provided for synthesizing information from multiple image series of different kernels into a single image series, and also for converting a single baseline image series of a kernel reconstructed by a CT scanner to image series of various other kernels, using deep-learning based methods. For multi-kernel synthesis, a single set of images with desired high spatial resolution and low image noise can be synthesized from multiple image series of different kernels. The synthesized kernel is sufficient for a wide variety of clinical tasks, even in circum-
(Continued)

stances that would otherwise require many separate image sets. Kernel conversion may be configured to generate images with arbitrary reconstruction kernels from a single baseline kernel. This would reduce the burden on the CT scanner and the archival system, and greatly simplify the clinical workflow.

8 Claims, 7 Drawing Sheets

(51) Int. Cl.
    G06F 18/21      (2023.01)
    G06F 18/214     (2023.01)
    G06N 3/08       (2023.01)
    G06T 11/00      (2006.01)
    G16H 30/20      (2018.01)
    G16H 30/40      (2018.01)
    G16H 50/20      (2018.01)

(52) U.S. Cl.
    CPC ............. *G06F 18/217* (2023.01); *G06N 3/08* (2013.01); *G16H 30/20* (2018.01); *G16H 30/40* (2018.01); *G16H 50/20* (2018.01); *G06T 2211/424* (2013.01)

(58) Field of Classification Search
    CPC .......... G06N 3/08; G16H 30/20; G16H 30/40; G16H 50/20
    See application file for complete search history.

(56) References Cited

U.S. PATENT DOCUMENTS

| 2006/0210131 | A1* | 9/2006 | Wheeler | G06T 11/008 382/128 |
|---|---|---|---|---|
| 2010/0246917 | A1* | 9/2010 | Bruder | A61B 6/482 382/131 |
| 2017/0206680 | A1 | 7/2017 | Tung | |
| 2018/0018757 | A1 | 1/2018 | Suzuki | |
| 2019/0035117 | A1* | 1/2019 | Xing | G06T 5/002 |
| 2019/0108634 | A1 | 4/2019 | Zaharchuk | |
| 2020/0043204 | A1* | 2/2020 | Fu | G06N 3/045 |

FOREIGN PATENT DOCUMENTS

| EP | 3576049 A2 | 3/2020 |
|---|---|---|
| WO | 2012168813 A1 | 12/2012 |

OTHER PUBLICATIONS

Chen, H., et al. "Low-dose CT denoising with convolutional neural network." 2017 IEEE 14th International Symposium on Biomedical Imaging (ISBI 2017). IEEE, 2017.

Chen, S. et al. "Towards automatic abdominal multi organ segmentation in dual energy CT using cascaded 3D fully convolutional network." arXiv preprint arXiv:1710.05379 (2017).

Dorn, S. et al. "Organ-specific context-sensitive single and dual energy CT (DECT) image reconstruction, display and analysis." 103rd Scientific Assembly and Annual Meeting of the Radiological Society of North America (RSNA). 2017.

He, K. et al., "Deep residual learning for image recognition," CoRR, vol. abs/1512.03385, 2015.

International Searching Authority. International Search Report and Written Opinion for application PCT/US2019/053756. Mailed on Mar. 17, 2020. 17 pages.

Kamil, M. Y. "Brain tumor area calculation in CT-scan image using morphological operations." IOSR Journal of Computer Engineering 17.2 (2015): 125-128.

McCollough C.H. et al. "Low-dose CT for the detection and classification of metastatic liver lesions: Results of the 2016 Low Dose CT Grand Challenge," Med Phys, vol. 44, No. 10, pp. e339-e352, Oct. 2017.

Sasidhar, B., et al. "Automated segmentation of lung regions using morphological operators in CT scan." Int. J. Sci. Eng. Res 4.9 (2013). 1114-1118.

Takagi, S., et al. "Combined multi-kernel head computed tomography images optimized for depicting both brain parenchyma and bone." Journal of X-ray science and technology 22.3 (2014): 369-376.

Weiss, K. L., et al. "Hybrid convolution kernel: optimized CT of the head, neck, and spine." American Journal of Roentgenology 196.2 (2011): 403-406.

Woo, I., et al. "Accuracy enhancement of CT kernel conversions using convolutional neural net for super-resolution with Squeeze-and-Excitation blocks and progressive learning among smooth and sharp kernels." MIDL Amsterdam (2018).

Xie, S. et al. "Aggregated residual transformations for deep neural networks," CoRR, vol. abs/1611.05431, 2016. Available: http://arxiv.org/abs/1611.05431.

Xue, Z., et al. (2012). Window classification of brain CT images in biomedical articles. In AMIA Annual Symposium Proceedings (vol. 2012, p. 1023). American Medical Informatics Association.

Yu, L. et al. "Development and validation of a practical lower-dose-simulation tool for optimizing computed tomography scan protocols," J Comput Assist Tomogr, vol. 36, No. 4, pp. 477-487, 2012.

* cited by examiner

SYSTEMS AND METHODS FOR MULTI-KERNEL SYNTHESIS AND KERNEL CONVERSION IN MEDICAL IMAGING

CROSS-REFERENCE TO RELATED APPLICATIONS

This application is a 371 U.S. National Phase application of PCT/US2019/053756, filed Sep. 28, 2019, which claims the benefit of U.S. Provisional Patent Application Ser. No. 62/738,764 filed on Sep. 28, 2018 and entitled "Systems and Methods for Multi-Kernel Synthesis and Kernel Conversion in Medical Imaging," which is herein incorporated by reference in its entirety.

STATEMENT REGARDING FEDERALLY SPONSORED RESEARCH

N/A

BACKGROUND

Computed tomography (CT) scanners differ substantially in x-ray sources, detectors, data acquisition systems, and reconstruction algorithms, but the general clinical workflow, including generating image series, image archival, retrieval, and display, remains very similar among most scanners. Images at different kernels (e.g., smooth, medium sharp, sharp, and the like), slice thicknesses, and intervals at different 3D planes are typically reconstructed from CT projection data. Some of these images can also be generated by 3D reformatting from already reconstructed images.

Selection of an appropriate reconstruction kernel is a step in reconstructing CT images that can greatly influence the appearance and clinical utility of the reconstructed image. That is, the choice of kernel can have a dramatic effect on the appearance of the reconstructed image. A very sharp kernel results in well-defined edges and high spatial resolution, but also amplifies image noise. On the other hand, a very smooth kernel reduces the noise, but comes at the cost of blurring sharp edges and fine anatomical details. This fundamental tradeoff means that diagnostic tasks may require multiple image sets, each reconstructed with different kernels, in order to evaluate all aspects of the images and achieve an accurate diagnosis.

Which image series is created depends on the clinical exams and diagnostic tasks. For example, trauma, musculoskeletal, thoracic and neurological CT exams can require ten or more separate reconstructions for a single patient scan, many of which use different kernel settings. It is not uncommon that some of the exams require many image series in a variety of configurations to be created and archived. Large numbers of image series being created and stored may put a huge burden on technologists, increase the burden on the archival system, increase reconstruction time, and slow down the scanner, which is problematic in a busy clinical environment. In addition, even if the exam protocol specifies a large number of image series to be generated at a variety of kernels and slice thicknesses, sometimes one would later like to have additional image series reconstructed in a manner that differs greatly from all images that have been archived. Since CT projection data are typically deleted from the scanner within a few days after the exam, it is unlikely that the data will be available to generate the needed image series at a later date.

One potential solution that could preserve the ability to reconstruct different kernel images at any time is to archive the CT projection data. There are many reasons why this is not feasible. First, CT projection data are usually large files that are difficult to transfer through a network. Second, most archival systems don't support the format of CT projection data, which are all encoded with proprietary information by the manufacturers of the CT systems. Most importantly, even if the CT projection data are available and can be interpreted correctly, the reconstruction system that is necessary to generate images from the projection data might not readily be available. This is because the reconstruction system is vendor and scanner-model specific and may be upgraded from time to time, making older projection data unusable.

Navigating and maintaining the plethora of available reconstruction kernels also creates numerous opportunities for errors, and therefore introduces a substantial burden on CT manufacturers, technologists, and radiologists reading CT images. There exists a need for both reducing the burden of multiple kernels and also for preserving the ability to generate different images with different kernels after the projection data has been lost.

SUMMARY OF THE DISCLOSURE

The present disclosure addresses the aforementioned drawbacks by providing a system and method for synthesizing information from multiple image series of different kernels into a single image series, and also for converting a single baseline image series of a kernel reconstructed by the scanner to image series of various other kernels, using deep-learning based methods. For multi-kernel synthesis, a single set of images with desired high spatial resolution and low image noise can be synthesized from multiple image series of different kernels. The synthesized kernel is sufficient for a wide variety of clinical tasks, even in circumstances that would otherwise require many separate image sets. This would significantly reduce the burden of dealing with multiple image sets for both technicians and radiologists. In one configuration, kernel conversion may be configured to generate images with arbitrary reconstruction kernels from a single baseline kernel. This would reduce the burden on the CT scanner and the archival system, and greatly simplify the clinical workflow, since only one single image series needs to be reconstructed by the scanner and archived, and all other kernels can be generated in an efficient manner as needed by specific clinical tasks.

In one configuration, a method is provided for synthesizing new image series from multiple image series. The method includes reconstructing at least two series of CT images, where the images are reconstructed with different reconstruction kernels. At least one new image series may be synthesized by subjecting the images to a neural network.

In one configuration, a method is provided for converting a single baseline kernel reconstructed by the scanner to image series of various other kernels. The method includes reconstructing a baseline CT image series using a kernel and generating at least one CT image series at another kernel by subjecting the baseline CT image series to a neural network.

In one configuration, a system is provided for converting a single baseline kernel reconstructed by the scanner to image series of various other kernels. The system includes a computer system configured to: reconstruct a baseline CT image series using a first kernel and to generate at least one CT image series at another kernel by subjecting the baseline CT image series to a neural network.

In one configuration, a method is provided for synthesizing and converting computed tomography (CT) kernels. The method includes reconstructing a baseline CT image series using a first kernel and generating at least two CT image series by subjecting the baseline CT image series to a neural network. At least one new image series may be synthesized by subjecting the two image series to a neural network. In some configurations, the two image series are reconstructed using different kernels.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

A system and method is provided for synthesizing information from multiple image series reconstructed with different kernels into a single image series, and also to generate image series with different kernels from a single image series reconstructed from the scanner. A single set of images may be synthesized with the best qualities of images reconstructed using multiple kernels that can be used for a wide variety of tasks. In addition, a method may employ deep learning-based systems, such as a deep convolutional neural network (CNN), to generate images with different kernels from one single image series reconstructed by the scanner with a sharp kernel. This method may be used to generate images at different kernels in just a fraction of the time it takes to run a full reconstruction, and may do so without using the raw projection data.

Although the advantages and disadvantages of smooth and sharp kernels are understood, it was not previously possible to combine the advantages of images reconstructed using different kernels into a single set of images. No generalized algorithm has previously been developed that is able to blend together images created with multiple kernels to produce an output image that matches or exceeds the clinical utility of each input image individually. Synthesizing information from multiple image series, each reconstructed with a different kernel, into a single image series allows for combining the advantages of different kernels. The application of an artificial neural network allows for circumventing the difficult task of determining hand selected rules for combining features in the input images. Instead of using predetermined rules, a network training procedure may determine how the input features should be merged to produce an optimal output image. Since the application of a trained neural network is very fast, this adds negligible computation time to the image reconstruction process, and opens up the possibility of applying the network in real time.

For the purposes of this disclosure and accompanying claims, the term "real time" or related terms are used to refer to and define a real-time performance of a system, which is understood as performance that is subject to operational deadlines from a given event to a system's response to that event. For example, a real-time extraction of data and/or displaying of such data based on empirically-acquired signals may be one triggered and/or executed simultaneously with and without interruption of a signal-acquisition procedure.

In some configurations, a convolutional neural network (CNN) may be trained to synthesize multiple input image series, each produced with a different reconstruction kernel, into a single output image series that exhibits improved image qualities (in terms of high sharpness and low noise levels) compared to each input individually. The CNN architecture may be based on any of a variety of selected design, such as a ResNet design, and may include repeated blocks of residual units with a plurality of layers, such as a total of 32 convolutional layers. The CNN inputs may include a selection from original images, such as images produced by soft (e.g., B10), medium-sharp (e.g., B45), and sharp (e.g., B70) kernels that may be stacked in the channel dimension. The CNN output may be treated as a perturbation that may be added to the sharp-kernel input, which may reduce the required training time. The network may be trained using supervised learning with full-dose images, reduced dose images, simulated images, such as simulated quarter-dose CT images, or other lower dose images, and the like. In some configurations, the full-dose images reconstructed with a sharp kernel may be used as the ground truth to evaluate a comparative loss function, such as with a mean squared error function.

Figure 1A:
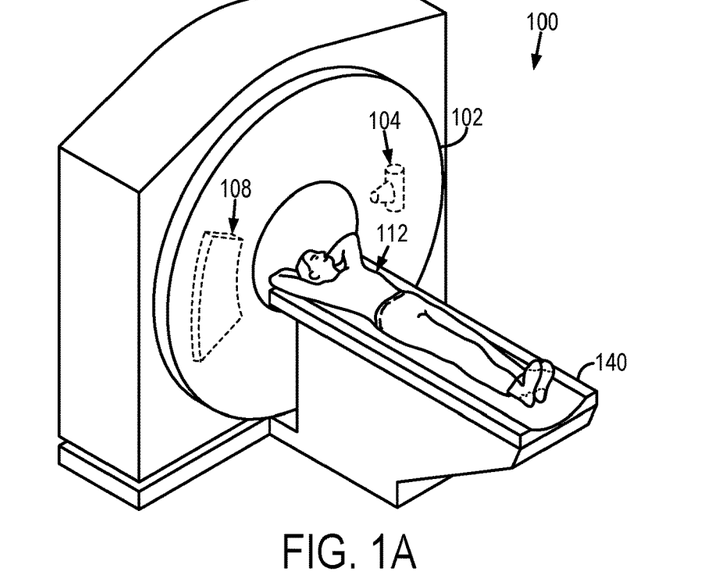
FIG. 1A illustrates an example CT system that can be configured to operate one configuration of the present disclosure.
Figure 1B:
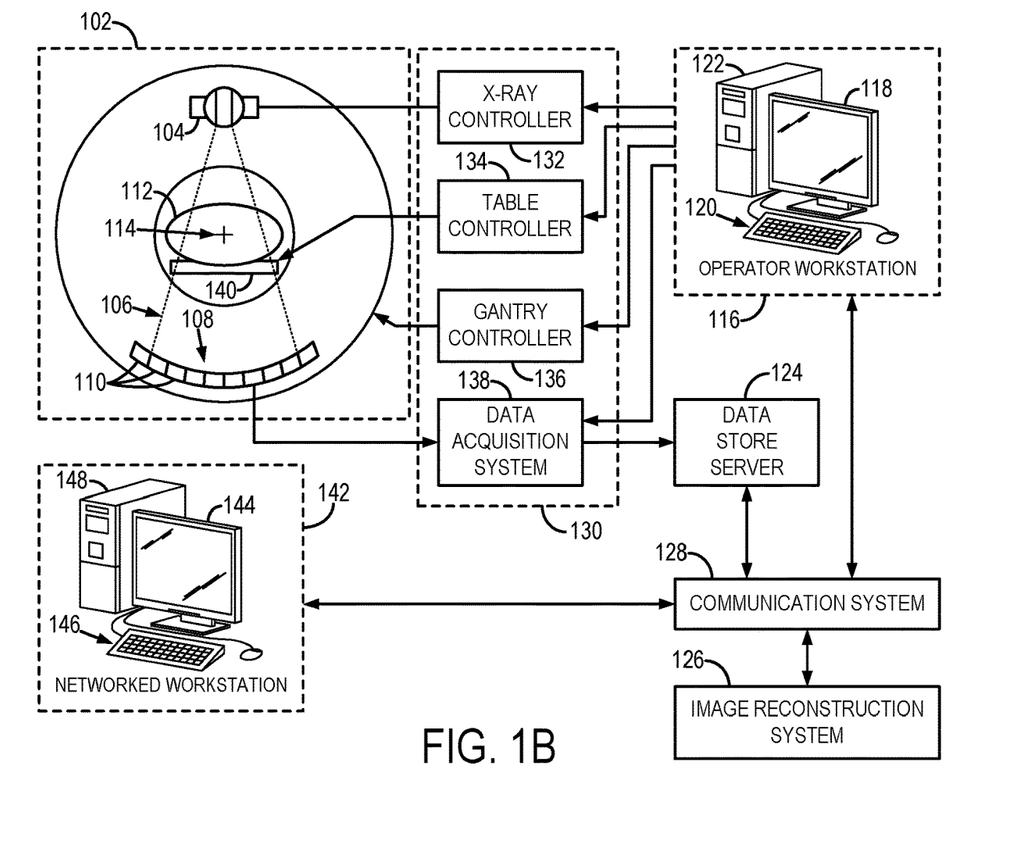
FIG. 1B is a schematic of one configuration for a system configured to operate the example CT system of FIG. 1A.

Referring particularly now to FIGS. 1A and 1B, an example of an x-ray computed tomography ("CT") imaging system 100 is illustrated. The CT system includes a gantry 102, to which at least one x-ray source 104 is coupled. The x-ray source 104 projects an x-ray beam 106, which may be a fan-beam or cone-beam of x-rays, towards a detector array 108 on the opposite side of the gantry 102. The detector array 108 includes a number of x-ray detector elements 110. Together, the x-ray detector elements 110 sense the projected x-rays 106 that pass through a subject 112, such as a medical patient or an object undergoing examination, that is positioned in the CT system 100. Each x-ray detector element 110 produces an electrical signal that may represent the intensity of an impinging x-ray beam and, hence, the attenuation of the beam as it passes through the subject 112. In some configurations, each x-ray detector 110 is capable of counting the number of x-ray photons that impinge upon the detector 110. In some configurations the system can include a second x-ray source and a second x-ray detector (not shown) operable at a different energy level than x-ray source 104 and detector 110. Any number of x-ray sources and corresponding x-ray detectors operable at different energies may be used, or a single x-ray source 104 may be operable to emit different energies that impinge upon detector 110. During a scan to acquire x-ray projection data, the gantry 102 and the components mounted thereon rotate about a center of rotation 114 located within the CT system 100.

The CT system 100 also includes an operator workstation 116, which typically includes a display 118; one or more input devices 120, such as a keyboard and mouse; and a computer processor 122. The computer processor 122 may include a commercially available programmable machine running a commercially available operating system. The operator workstation 116 provides the operator interface that enables scanning control parameters to be entered into the CT system 100. In general, the operator workstation 116 is in communication with a data store server 124 and an image reconstruction system 126. By way of example, the operator workstation 116, data store sever 124, and image reconstruction system 126 may be connected via a communication system 128, which may include any suitable network connection, whether wired, wireless, or a combination of both. As an example, the communication system 128 may include both proprietary or dedicated networks, as well as open networks, such as the internet.

The operator workstation 116 is also in communication with a control system 130 that controls operation of the CT system 100. The control system 130 generally includes an x-ray controller 132, a table controller 134, a gantry controller 136, and a data acquisition system 138. The x-ray controller 132 provides power and timing signals to the x-ray source 104 and the gantry controller 136 controls the rotational speed and position of the gantry 102. The table controller 134 controls a table 140 to position the subject 112 in the gantry 102 of the CT system 100.

The DAS 138 samples data from the detector elements 110 and converts the data to digital signals for subsequent processing. For instance, digitized x-ray data is communicated from the DAS 138 to the data store server 124. The image reconstruction system 126 then retrieves the x-ray data from the data store server 124 and reconstructs an image therefrom. The image reconstruction system 126 may include a commercially available computer processor, or may be a highly parallel computer architecture, such as a system that includes multiple-core processors and massively parallel, high-density computing devices. Optionally, image reconstruction can also be performed on the processor 122 in the operator workstation 116. Reconstructed images can then be communicated back to the data store server 124 for storage or to the operator workstation 116 to be displayed to the operator or clinician.

The CT system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 116, or in a different facility, such as a different healthcare institution or clinic.

The networked workstation 142, whether within the same facility or in a different facility as the operator workstation 116, may gain remote access to the data store server 124 and/or the image reconstruction system 126 via the communication system 128. Accordingly, multiple networked workstations 142 may have access to the data store server 124 and/or image reconstruction system 126. In this manner, x-ray data, reconstructed images, or other data may be exchanged between the data store server 124, the image reconstruction system 126, and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Figure 2:
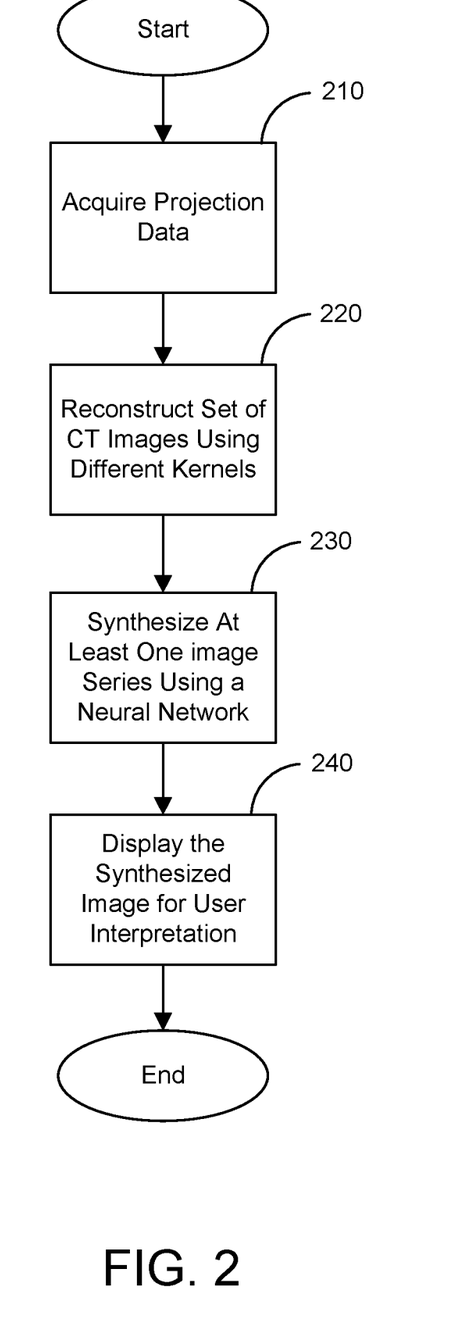
FIG. 2 is a flow chart setting forth some non-limiting examples of steps for a method for performing a multi-kernel synthesis in accordance with the present disclosure.

Referring to FIG. 2, a flowchart setting forth some non-limiting examples of steps for performing a multi-kernel synthesis is shown. Beginning at step 210, raw projection data of a subject is acquired. This may include performing a CT scan of the subject or accessing previously-acquired or stored data. A set of CT images is reconstructed at step 220 where the images are reconstructed using different kernels. In some configurations of the multi-kernel synthesis method, the set of CT images may be fixed beforehand to span a range of spatial resolution and noise that may be synthesized according to the steps below. In some configurations, the set of CT images may be images that have been defined by a medical professional, such as a radiologist, that may be selected to represent a broad range of tissue types, such as soft tissues in one image and bones in another image in the set. In some configurations, the set of CT images may be images selected based upon case specific criteria, such as the need to visualize a certain region of interest, or to emphasize contrast between regions of interest. In some configurations, the set of CT images may be reconstructed using different image kernels that may be determined based upon desired contrast to noise ratio, signal to noise ratio, dose level, and the like. At step 230, the set of CT images may be subjected to a neural network that synthesizes a single image series, or a selected number of synthesized images, from the original fixed set of images. At step 240, a synthesized image or images may be displayed for a user, such as a radiologist, for interpretation. The synthesized image or images may also be stored in a computer archive for future use.

In some configurations, a network training procedure may determine how the input image features should be merged to produce an optimal output image. The optimization may be performed to create a single image series where different kernels have been mixed together to emphasize certain features or regions of interest in an image, such as mixing a soft kernel and a sharp kernel to form an optimized single image. In some configurations, an optimization may be performed using deep learning methods to model a function that combines image features in a way that is desirable with regards to a specified loss function. In some configurations, the synthesized image may be a single image and may be a combination of the best image qualities of multiple kernels. Image qualities may include spatial resolution, contrast-to-noise ratio, and signal-to-noise ratio.

In some configurations, the method used to generate data to train the neural network includes supervised learning. In order to use supervised learning, a training dataset may be generated that includes input images, each paired with the desired output. Since the desired output, such as a map of the X-ray attenuation coefficients of the imaged object, may be unknown, and the input CT images may be an approximation of this quantity, generating a useful training dataset may not be a simple task. In some configurations to create a dataset, the input images may be degraded by artificially inserting CT image noise, thereby allowing the original CT images to be used as examples of superior image quality. After the neural network has been trained to combine the input images in a desired way, it can then be applied to unaltered clinical images.

Figure 3:
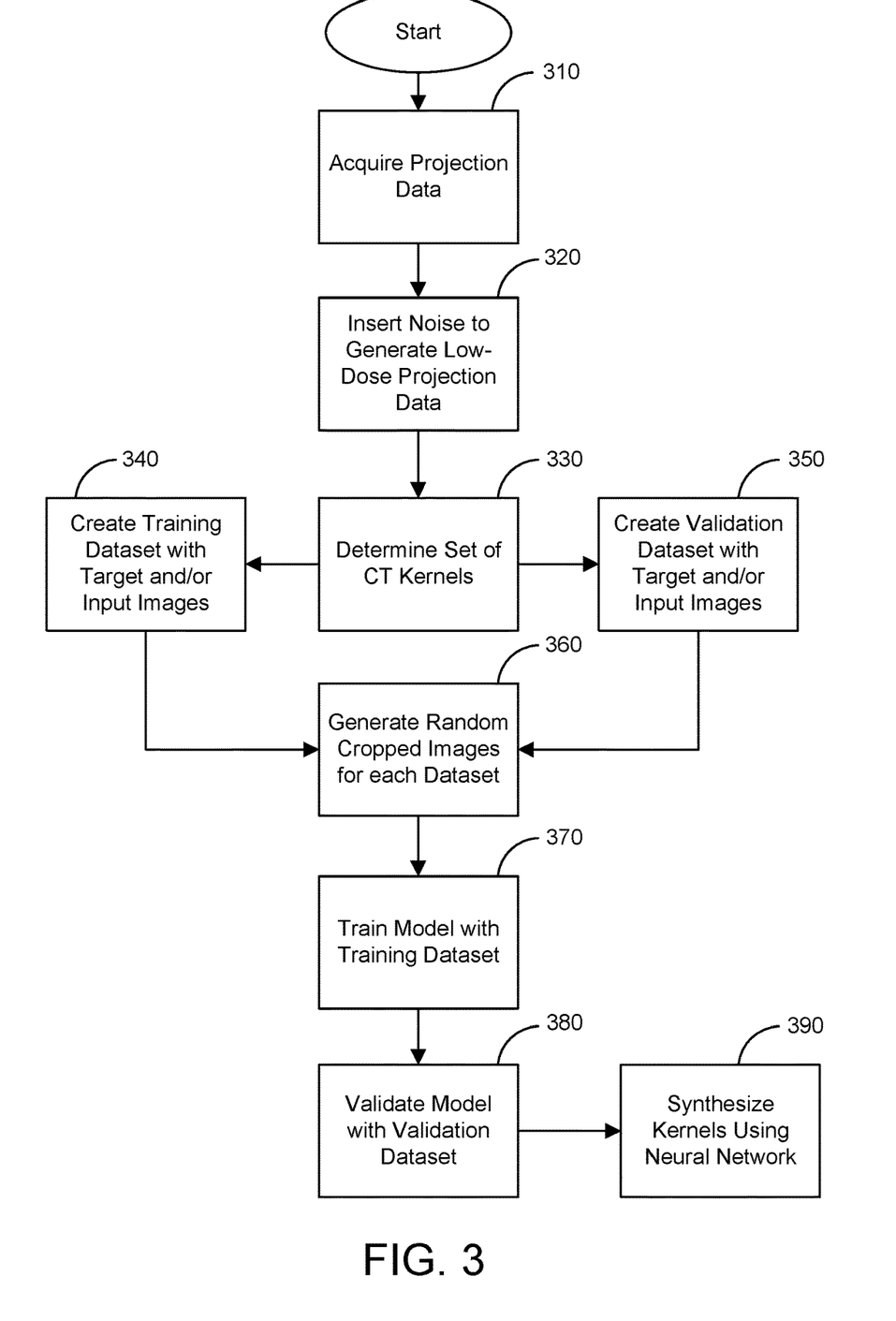
FIG. 3 is another flow chart setting forth some non-limiting examples of steps for a training method in accordance with the present disclosure.

Referring to FIG. 3, one configuration for a training procedure for a neural network configured to perform kernel synthesis is shown. CT scan projection data is acquired at step 310. Again, this data may be acquired by performing an imaging process or by accessing stored data. The acquired projection data, preferably, has a desirable signal-to-noise ratio, such as may be achieved using a "full dose" of radiation when acquiring the data. By inserting noise into the data, a low-dose projection dataset may be generated at step 320. A set of CT kernels may be determined at step 330. A training dataset may be created at step 340 and contain target images and/or input images. A validation set may be created at step 350 and contain target images and/or input images. Target images may be formed of regions of interest of a subject depicting disease, pathology, or any other area of interest in a specified kernel, and may be full-dose images, reduced dose images, simulated images, such as simulated quarter-dose CT images, or other lower dose images, and the like. Input images may be any arbitrarily-sized stack of images with a number of adjacent slices in the channel dimension, and may be the full-dose or other high-signal-to-noise-ratio images, reduced dose images, simulated images, such as simulated quarter-dose CT images, or other lower dose images, and the like. Random cropped images may be generated for the training dataset and the validation dataset at step 360. A neural network model may then be trained at step 370 with the training dataset. The trained neural network model may be validated by comparing results with the validation dataset at step 380. Synthesized kernels may be created using the trained neural network at step 390, and the trained neural network may be used in a process according to FIG. 2.

Figure 4:
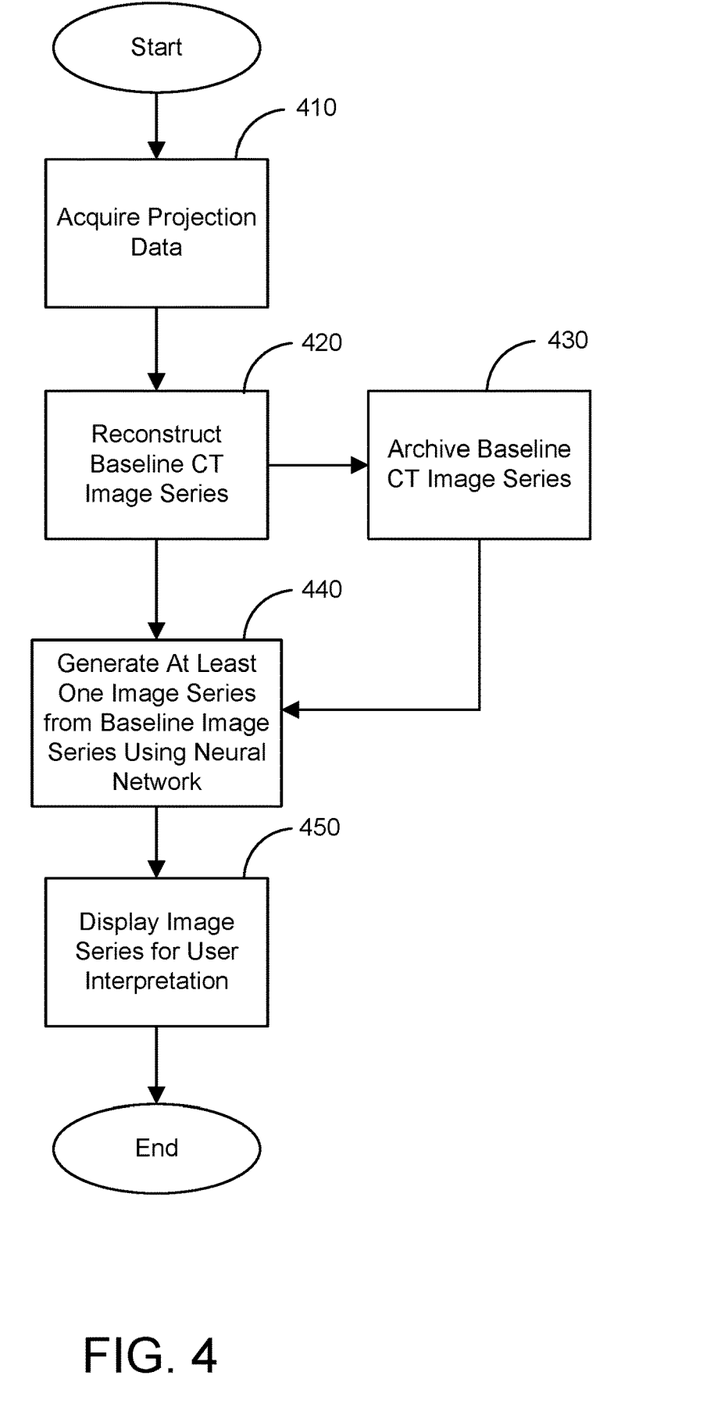
FIG. 4 is yet another flow chart setting forth some non-limiting examples of steps for a method of generating image series with arbitrary kernels from one single baseline image series in accordance with the present disclosure.

Referring to FIG. 4, a flowchart is shown for one configuration of generating image series at multiple kernels from a single baseline CT image series. A raw projection data is acquired at step 410. This may be achieved by performing a CT imaging scan or by accessing stored data. A baseline CT image or image series is reconstructed at 420, and may be stored in a long-term archival system at step 430. This baseline image or image series may be used to provide a basis upon which other images may be generated without needing to retain the original raw projection data. In one configuration, the baseline CT image series is a sharp kernel with a thin slice thickness (such as the sharpest the system can provide), which is assumed to retain most, if not all, of the information in the acquired data. Image series of new kernels may be generated at step 440 based on this baseline image series as needed. The generated image series may then be displayed for a user at step 450 according to specific exam protocols.

In some configurations, the baseline image is a single image reconstruction and may be in the sharpest possible spatial resolution that is determined by the data acquisition and in a sufficiently large matrix size to avoid aliasing. In some configurations, the spatial resolution can be lower than these limits and the matrix size can be smaller to save storage space, provided that all the clinically required kernels can still be generated by this one single image series.

In current clinical workflows, many reconstruction jobs are needed to be done on the scanner by the image reconstruction system (IRS). Often, some of the reconstructions or reformats need to be manually performed by the technologists before sending to the PACS or long-term archival systems. This workflow is an inefficient use of scanner and technologist time, especially in a busy working environment. The process described with respect to FIG. 4 provides one method for improving clinical workflow using a deep learning-based method. In one configuration, the scanner reconstructs and archives only one single image series from the CT projection data. A deep learning-based neural network system, together with other image processing methods, may be employed to generate image series at other spatial resolutions, slice thicknesses, and 3D reformatted planes. This may substantially increase the efficiency of scanner utilization and technologist time, reduce the burden on the archival system, and simplify the clinical workflow.

In some configurations, various image series of different kernels can either be generated in real time based on the request from the human reader or pre-generated based on a specific protocol for the diagnostic task and loaded on an image storage system, such as the PACS, or other image viewers for diagnosis. In one non-limiting example, the list of reconstruction jobs can be pre-generated on the workstation by the CNN (and 3D reformat tool) and displayed automatically after the exam is loaded for diagnosis. Additional kernels can be generated as requested, which may be much faster than image reconstructions performed from raw data. Generating various image series of different kernels may not require vendor-specific software.

In some configurations, the neural network is trained prior to being used to generate new image series of different kernels. During the training of the network, the training images can be at a higher dose so that the neural network can be trained to generate a new image series with a noise reduction effect.

In some configurations, the newly generated image output of the neural network at step 440 of FIG. 4 may not need to mimic exactly an existing kernel. New image series with a tradeoff between spatial resolution and noise that is different from existing kernels can also be generated, such as by simulating an image created from a blend of kernels. This may also offer the opportunity of creating vendor neutral kernels from different scanner makes and models.

Figure 5:
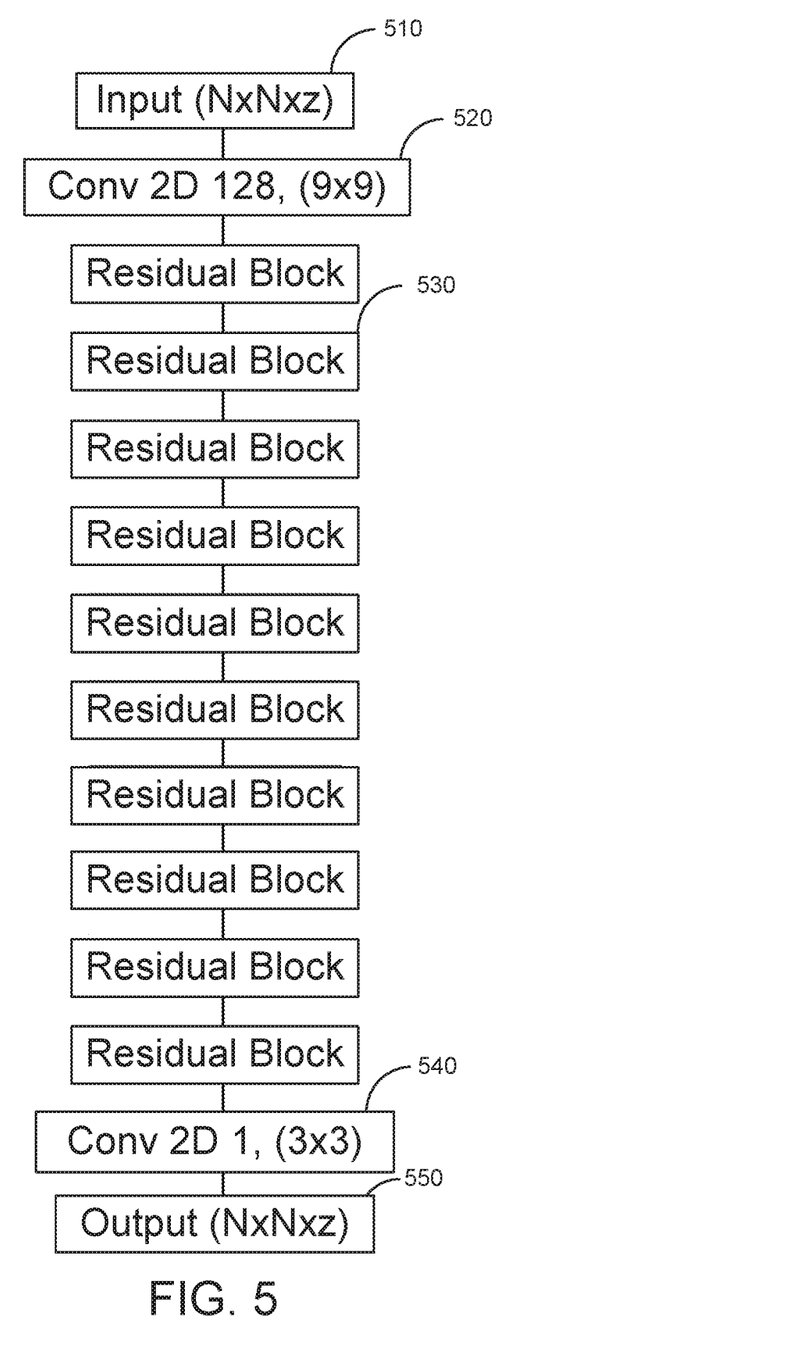
FIG. 5 is a schematic diagram of one example of a convolutional neural network architecture in accordance with the present disclosure.

Referring to FIG. 5, one non-limiting example convolutional neural network architecture is shown. An input image 510 may be any arbitrarily-sized stack of images, with a fixed number of adjacent slices in the channel dimension. In one non-limiting example, the input image 210 is a sharp kernel. In some configurations, the input image 510 may be three arbitrarily-shaped images, each from a different reconstruction kernel, stacked in the channel dimension. A convolution layer 520 may be one of a plurality of layers, such as one of a 32 layer convolutional neural network. A residual block 530 may be one of a plurality of blocks, such as 10 blocks in one non-limiting example, containing a plurality of convolutional layers and filters, and are detailed below. A final convolution layer 540 may perform a final process before generating an output 550. The output 550 may be a single-channel image that can be identified as a perturbative correction for the input image, such as the sharpest kernel. In some configurations, the input image 510 may be subjected to a convolutional neural network where a predicted noise correction is determined so that noise can be subtracted from a network processed image to create an output image 550, which may then be compared to a full-dose reference.

Figure 6:
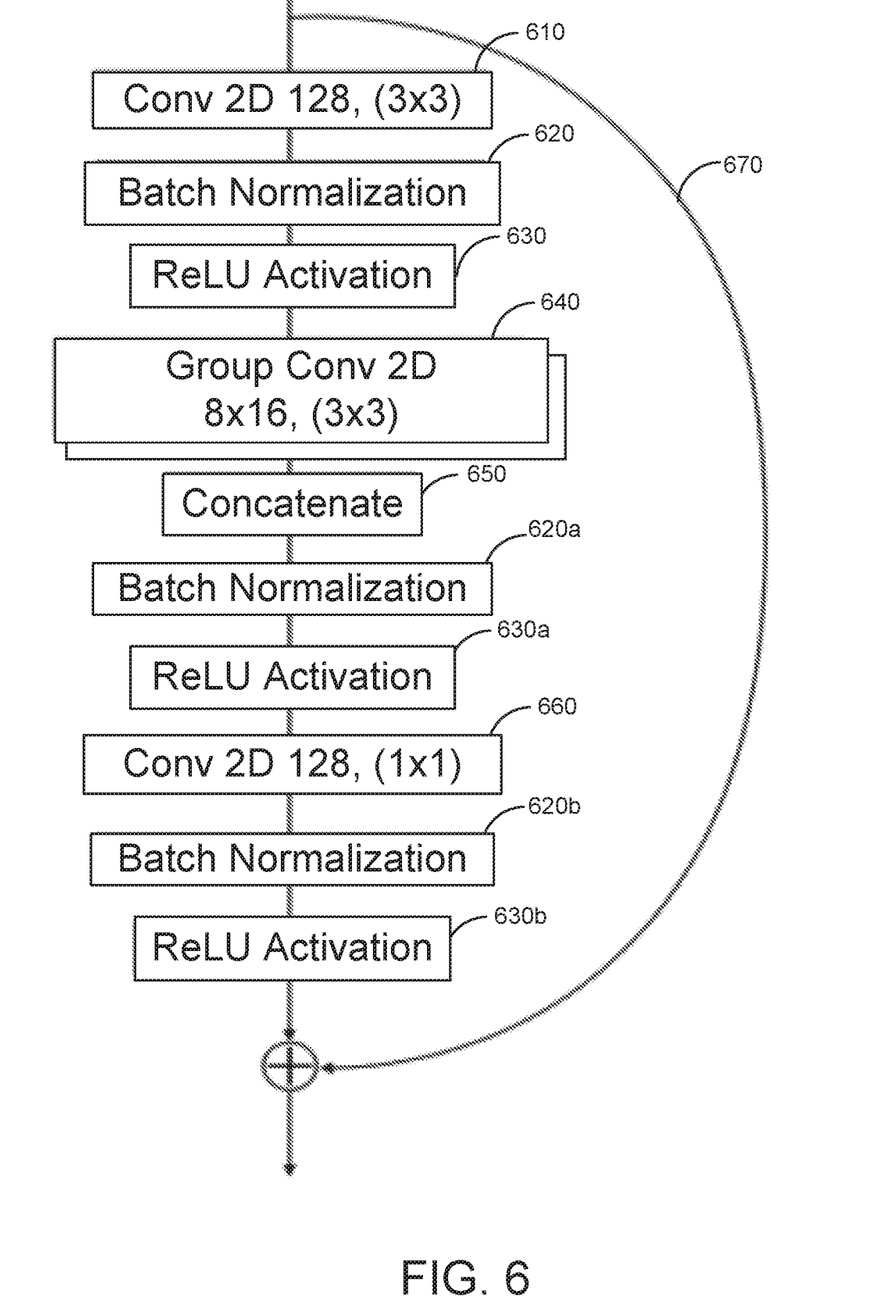
FIG. 6 is a schematic diagram of a residual block structure in accordance with the present disclosure.

Referring to FIG. 6, an example of a residual block structure from FIG. 5 is shown in detail. An example residual block may include multiple convolutional layers with multiple filters each. In one, non-limiting example, 3 convolutional layers having 128 filters each may be used. A convolutional layer 610 may be followed by a batch normalization process 620. An activation function 630, such as a rectified linear unit (ReLU) activation function, may be used to determine when a feature is considered to be significant. A second convolutional layer 640 may be one of a plurality of convolutional procedures. Data may be consolidated with concatenation 650. A final convolution layer 660 may then project back into the image domain. The specific number of convolutional layers may vary between implementations. Following each convolutional layer, respective batch normalizations 620a, 620b and activations 630a, 630b may be included. A bypass 670 indicates that a particular residual block may be skipped if the appropriate criteria are met. To preserve spatial resolution, no pooling or other downsampling operations were used.

Execution time may vary depending on hardware and the exact CNN architecture used. In some configurations, an easier kernel conversion may be able to use a smaller CNN (fewer residual blocks). In one non-limiting example, time to process a single scan slice was 0.17 sec. for kernel synthesis and 0.02 sec.-0.17 sec. for kernel conversion using commercially available graphical processing unit (GPU) hardware. A CNN may be implemented in any appropriate coding language, such as Python, and may be trained using any appropriate tools, including open-source tools (such as Tensorflow) and standard Python scientific computing packages. CNN architecture may be selected to be similar to image classification networks (such as ResNet), for ease of commercial deployment.

Example Multi-Kernel Synthesis

In one non-limiting example, simulated quarter-dose images obtained from different kernels were used as the network input, and the corresponding full-dose images reconstructed with the sharp kernel were used as the ground truth to evaluate a mean-squared-error loss function. The network was trained on 500,000 example images of various sizes that were cropped from ten abdominal CT exams. After training, the performance was evaluated by comparing input and output images using a reserved set of full-dose abdominal, chest, and phantom CT scans that were not used in the network training.

Images were combined from three input kernels: a very sharp kernel (e.g., Siemens B70), a very smooth (e.g., Siemens B10), and an intermediate kernel (e.g., Siemens B45). The resultant images maintain the sharp edges and fine anatomical details of the sharpest input kernel, while also exhibiting the low noise characteristics and maintaining the ability to identify subtle anatomical details of the smooth kernels. For images acquired with low dose level (one quarter of clinical dose), the signal-to-noise ratio of in the sharp kernel images is increased by over 200%, thereby potentially making these images clinically useful. Different tissues that require specific kernels for optimal viewing, such as bones, liver and lungs, all appear to have satisfactory quality in the resultant image. Furthermore, the images are devoid of any artificial textures that detract from the natural appearance of the images.

The synthetic images in the current example improved the signal-to-noise ratio by 338% compared to the sharp kernel images, without observable blurring of sharp edges. Despite the increased smoothness, the synthesized image maintains many of the sharp features and fine details contained in the sharpest input images. The synthesized images also appear natural, with no perceptible artificial texture introduced that detracted from the natural appearance of the synthetic image. The algorithm was robust enough to be applied to multiple tissue types, including the bones, lungs, and liver.

Example Kernel Conversion from a Single Baseline Image Series

In one non-limiting example of how a deep learning-based method can be used to generate multiple reconstruction kernels from a single high-resolution baseline image series, a deep CNN was trained using supervised learning on clinical CT images reconstructed with the sharpest available kernel (an S80 kernel on a Siemens Flash scanner) with thin slices (0.6 mm) to preserve information acquired in the raw data, as inputs. Using a very sharp kernel ensures that all useful information from the data acquisition is included in the input image series.

Three commonly-used body CT target kernels were generated with a CNN approach: a smooth kernel (B30), medium-sharp kernel (B46), and sharp kernel (B70). A separate CNN training was performed for each kernel. For each kernel, the full training dataset consisted of 250,000 paired 64×64 pixel images randomly cropped from the base kernel images and target kernel images. A supervised learning approach was used, with the loss function defined as the mean squared error (MSE) between the CNN-generated kernel image and the truly reconstructed target kernel image. The CNN was implemented with Tensorflow. The approach was tested on a reserved set of 20 clinical patient scans that were not used for network training. Accuracy of the approach was determined by subtracting the simulated kernel images from the target kernel images. Additionally, the mean absolute error was calculated on a pixel by pixel basis for each case.

After training for 100 epochs, the result was tested on a patient scan not included in the training data. The CNN simulates the appearance of other kernels to an almost imperceptible level of accuracy. The mean absolute difference between the images generated with the trained CNN and the actually reconstructed images was 2.0 HU for the B30 kernel, and 3.1 HU for the B46 kernel. Any reconstruction kernels can be generated, including iterative reconstruction. By training with high-dose image series, noise reduction effect can be inherently included in the kernel conversion. By converting baseline image series to images reconstructed with iterative reconstruction, similar image quality improvement as by iterative reconstruction may be achieved. Artifact correction may have already been implemented in the baseline image series.

Non-Limiting Example Individualized Denoising

Figure 7:
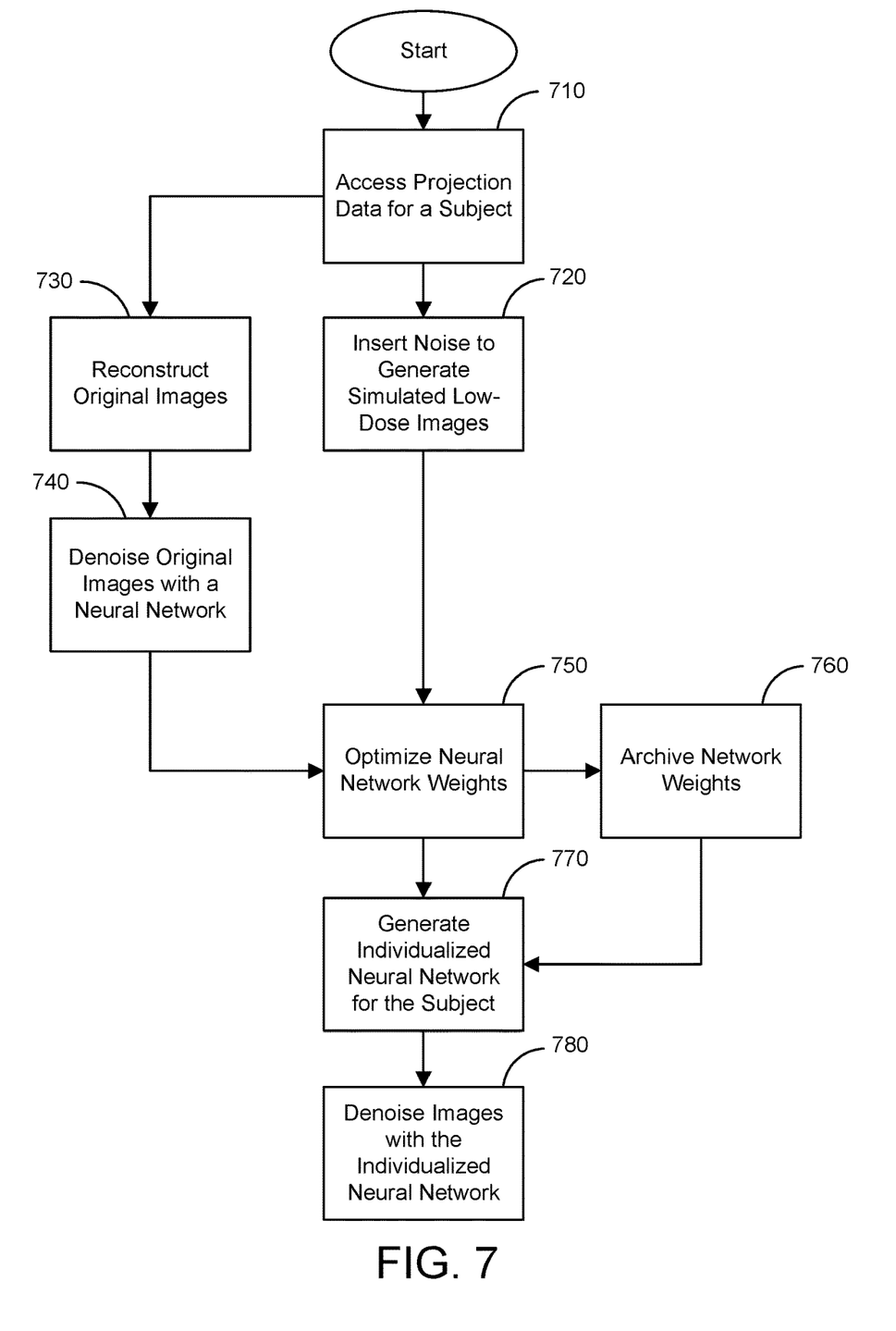
FIG. 7 is a flow chart setting forth some non-limiting example steps for individualized image denoising in accordance with the present disclosure.

Referring to FIG. 7, non-limiting example steps for individualized image denoising are shown, which may be used with the present disclosure. Raw image data, such as CT projection data, may be acquired or accessed at step 710. Noise may be introduced to the data as described above to generate simulated low-dose images at step 720. Original images that do not include introduced noise may be reconstructed at step 730. These original images may be denoised with a neural network at step 740. Neural network weights, such as weights for a CNN, may be optimized at step 750 using the simulated low-dose images as described above, or the original images, or a combination of both, such as during a comparison of the images. The neural network weights in step 750 may be archived at step 760, such as for future use, reference, review, and the like. A neural network that may be optimized specifically for the individual subject may be generated at step 770 using the weights from step 750, or those archived at step 760. In some configurations, the neural network used in step 770 may be a different neural network than that used in step 740. Denoised images with the individualized neural network may be generated at step 780.

The present disclosure has described one or more preferred embodiments, and it should be appreciated that many equivalents, alternatives, variations, and modifications, aside from those expressly stated, are possible and within the scope of the invention.

The invention claimed is:

1. A method for synthesizing computed tomography (CT) image series comprising:
   a) accessing projection data acquired from a subject using a CT system;
   b) reconstructing at least a first CT image series from the projection data using a first reconstruction kernel associated with a first set of image qualities and a second CT image series from the projection data using a second reconstruction kernel associated with a second set of image qualities; and
   c) synthesizing at least one new CT image series by subjecting the at least first and second CT image series to an artificial neural network, the at least one new CT image series being characterized by a combination of the first set of image qualities and the second set of image qualities.

2. The method of claim 1 wherein the first set of image qualities and the second set of image qualities include at least one of spatial resolution, noise, contrast to noise ratio, or signal to noise ratio.

3. The method of claim 1 further comprising optimizing the at least one new CT image series by minimizing a loss function with the neural network.

4. The method of claim 1 wherein the different reconstruction kernels include a soft kernel and a sharp kernel.

5. The method of claim 1 wherein the synthesized at least one new CT image series includes a higher signal to noise ratio than the at least two CT image series.

6. The method of claim 1 further comprising training the neural network wherein a training dataset is created by inserting noise into full-dose CT data to create low-dose CT data.

7. The method of claim 6 further comprising validating the neural network training by comparing the synthesized at least one new CT image series with the full-dose images.

8. The method of claim 1 further comprising displaying the synthesized at least one new CT image series for a user.

* * * * *